United States Patent [19]

Shoberg et al.

[11] Patent Number: 5,586,629

[45] Date of Patent: Dec. 24, 1996

[54] PRESURE CONTROLLED SYSTEM FOR FILLING AN IMPLANTABLE DRUG INFUSION PUMP

[75] Inventors: Bret R. Shoberg, Corcoran; Kenneth T. Heruth, Maple Grove, both of Minn.

[73] Assignee: Medtronic, Inc., Minneapolis, Minn.

[21] Appl. No.: 422,362

[22] Filed: Apr. 13, 1995

[51] Int. Cl.$^6$ .................. B65B 1/04; B65B 3/04
[52] U.S. Cl. .................. 141/21; 141/25; 141/192; 604/65; 604/237
[58] Field of Search .................. 141/21, 25, 26, 141/27, 98, 192; 137/505.38, 505.44; 604/65, 67, 82, 236, 237, 246, 247

[56] References Cited

U.S. PATENT DOCUMENTS

| | | | |
|---|---|---|---|
| 3,650,699 | 3/1972 | Beer | 141/25 |
| 4,074,694 | 2/1978 | Lee | 137/505.38 |
| 4,606,371 | 8/1986 | Maekawa | 137/505.38 |
| 5,158,547 | 10/1992 | Doan et al. | 604/93 |

*Primary Examiner*—Henry J. Recla
*Assistant Examiner*—Steven O. Douglas
*Attorney, Agent, or Firm*—Curtis D. Kinghorn; Harold R. Patton

[57] ABSTRACT

An implantable drug infusion pump filling system includes a filling syringe, a pressure control valve, a filling tube, and an implantable drug infusion pump. The pressure of the drug or agent loaded into the pump is prevented from exceeding a selected maximum pressure by the pressure control valve. The pressure control valve comprises a valve body that has an inlet passage coupled to the filling syringe, an internal chamber, and a discharge passage coupled to the pump. The inlet passage, the internal chamber, and the discharge passage form a flow passage for the flow of the drug. A mandrel is slidably disposed in the valve body. The mandrel is coupled to a flexible membrane, which is, in turn, coupled to a biasing member. When the pressure of the drug or agent acting on the flexible membrane exceeds the spring constant of the biasing member, the mandrel moves to a closed position, shutting off the flow passage.

13 Claims, 5 Drawing Sheets

5,586,629

1

PRESURE CONTROLLED SYSTEM FOR FILLING AN IMPLANTABLE DRUG INFUSION PUMP

BACKGROUND OF THE INVENTION

1. Field of the Invention

This invention relates generally to systems for filling an implantable drug infusion pump. More particularly, the invention relates to a system for filling an implantable drug infusion pump whereby the pressure of the fluid delivered into the pump is controlled to avoid potentially damaging over-pressurization of the pump.

2. Description of the Related Art

The implantable drug infusion pump (IDIP) has provided physicians with a powerful tool for administering a wide variety of drugs and other agents, such as nerve growth factor, to very particularized sites within a patient's body, such as the intrathecal region of the spinal column. The IDIP has also freed some patients from the restrictions of typical intravenous drug infusion systems that typically include a wheeled cart that must be pulled around behind the patient.

An IDIP is ordinarily surgically implanted subcutaneously in the patient's abdomen. The IDIP has an internal reservoir for storing the drug or agent. After implantation, the drug or agent is delivered to a selected site in the patient's body via a catheter that is attached to the pump and tunneled subcutaneously to the selected site. Many medical applications calling for an IDIP require very minute dosages or drug or agent to be delivered to the selected site over a period of time. For example, dosages of 100 µl over a span of twenty-four hours are not uncommon. IDIPs that are capable of delivering such minute quantities of drug or agent are sensitive to, and may be damaged by, over-pressurization of the reservoir.

Before the IDIP can be implanted in the patient's body, it must be filled with the applicable drug or agent. For some long-term applications, the IDIP may have to be refilled while the pump is still implanted within the patient's body. This is normally done by passing the drug or agent through a hypodermic needle that has been pierced through the patient's skin and coupled to the subcutaneously disposed IDIP. During these filling and refilling procedures, there is the risk that the pump's reservoir will become over-pressurized, possibly damaging the pump or affecting its performance.

Previous systems for filling or refilling an IDIP have utilized some type of pressure monitor to enable the technician to monitor the pressure of fluid delivered to the pump during filling. An example of such a prior art system is shown in FIG. 1. The prior art system 10 includes a filling syringe 12, a pressure monitor 14, a filling tube 16, and an IDIP 18. The inlet 20 of the pressure monitor 14 is coupled to the discharge outlet 22 of the filling syringe 12. The discharge orifice 24 of the pressure monitor is coupled to the inlet end 26 of the filling tube 16. As the plunger 28 of the syringe is depressed, drug flows from the syringe 12 through the pressure monitor 14 and the filling tube 16 and into the pump 18. The prior art system 10 has a notable disadvantage. Due to pressure loss in the system 10, the pressure monitor 14 will only indicate the pressure of the fluid in the pump 18 after the pump 18 has been filled and the flow of drug has stopped. Consequently, if the pump 18 has been accidentally over-filled, the pump may be over-pressurized and possibly damaged before the technician is made aware of the pressure level in the pump 18 by the pressure monitor 14. At that point, the pump 18 may be irreparably damaged.

The present invention is directed to overcoming the aforementioned disadvantage.

SUMMARY OF THE INVENTION

In one aspect of the present invention, a pressure controlled system for filling a drug infusion pump comprises a filling syringe, a pressure control valve coupled to the filling syringe and in fluid communication therewith. The pressure control valve is adapted to couple to the drug infusion pump. The pressure control valve comprises a valve body and a flow passage extending therethrough. A flexible membrane is disposed within the valve body. The flexible membrane has a surface in fluid communication with the flow passage. The flexible membrane is operable to expand and contract in response to pressure in the flow passage. A mandrel is coupled to the flexible membrane. The mandrel has a first open position and a second closed position, and is operable to move to the closed position to close the flow passage when the flexible membrane is expanded a preselected amount. A biasing member is operable to bias the mandrel toward the open position.

In another aspect of the present invention, a pressure control valve comprises a valve body, a flow passage extending through the valve body, and a flexible membrane disposed within the valve body. The flexible membrane has a first surface in fluid communication with the flow passage, and is operable to expand and contract in response to pressure in the flow passage. A mandrel is coupled to the flexible membrane. The mandrel has a first open position and a second closed position, and is operable to move to the closed position to close the flow passage when the flexible membrane is expanded a preselected amount. A biasing member is operable to bias the mandrel toward the open position.

In another aspect of the present invention, a pressure controlled drug infusion pump filling system comprises an infusion pump, a filling syringe, and a pressure control valve that is coupled to the filling syringe and the pump and that is in fluid communication therewith. The pressure control valve comprises a valve body and a flow passage extending therethrough. A flexible membrane is disposed within the valve body. The flexible membrane has a surface in fluid communication with the flow passage. The flexible membrane is operable to expand and contract in response to pressure in the flow passage. A mandrel is coupled to the flexible membrane. The mandrel has a first open position and a second closed position, and is operable to move to the closed position to close the flow passage when the flexible membrane is expanded a preselected amount. A biasing member is operable to bias the mandrel toward the open position.

BRIEF DESCRIPTION OF THE DRAWINGS

Advantages of the invention will become apparent upon reading the following detailed description and references to the drawings in which.

DESCRIPTION OF THE PREFERRED EMBODIMENT

Figure 1:
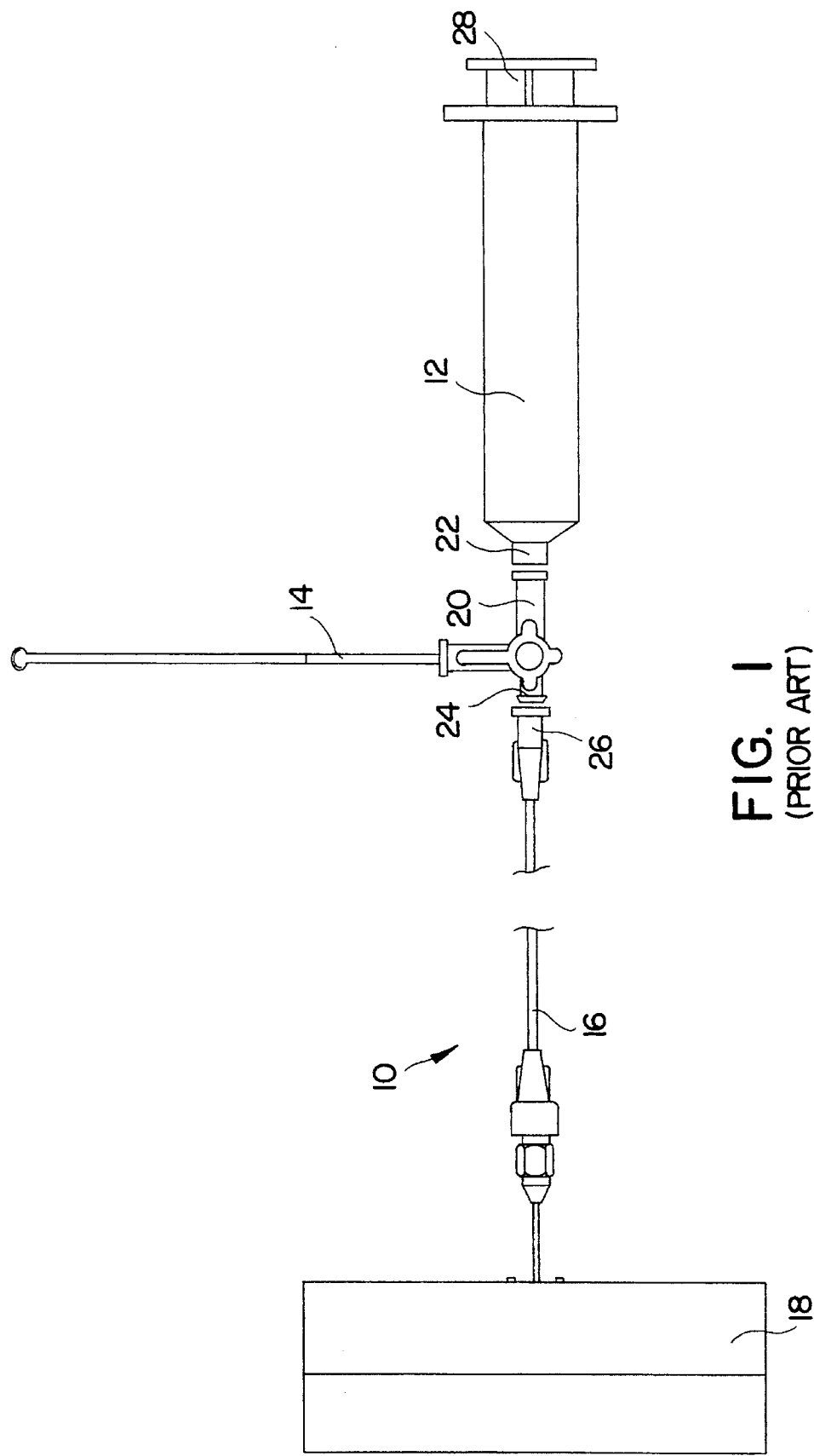
FIG. 1 depicts an exemplary prior art IDIP filling system, illustrated in a front view.
Figure 2:
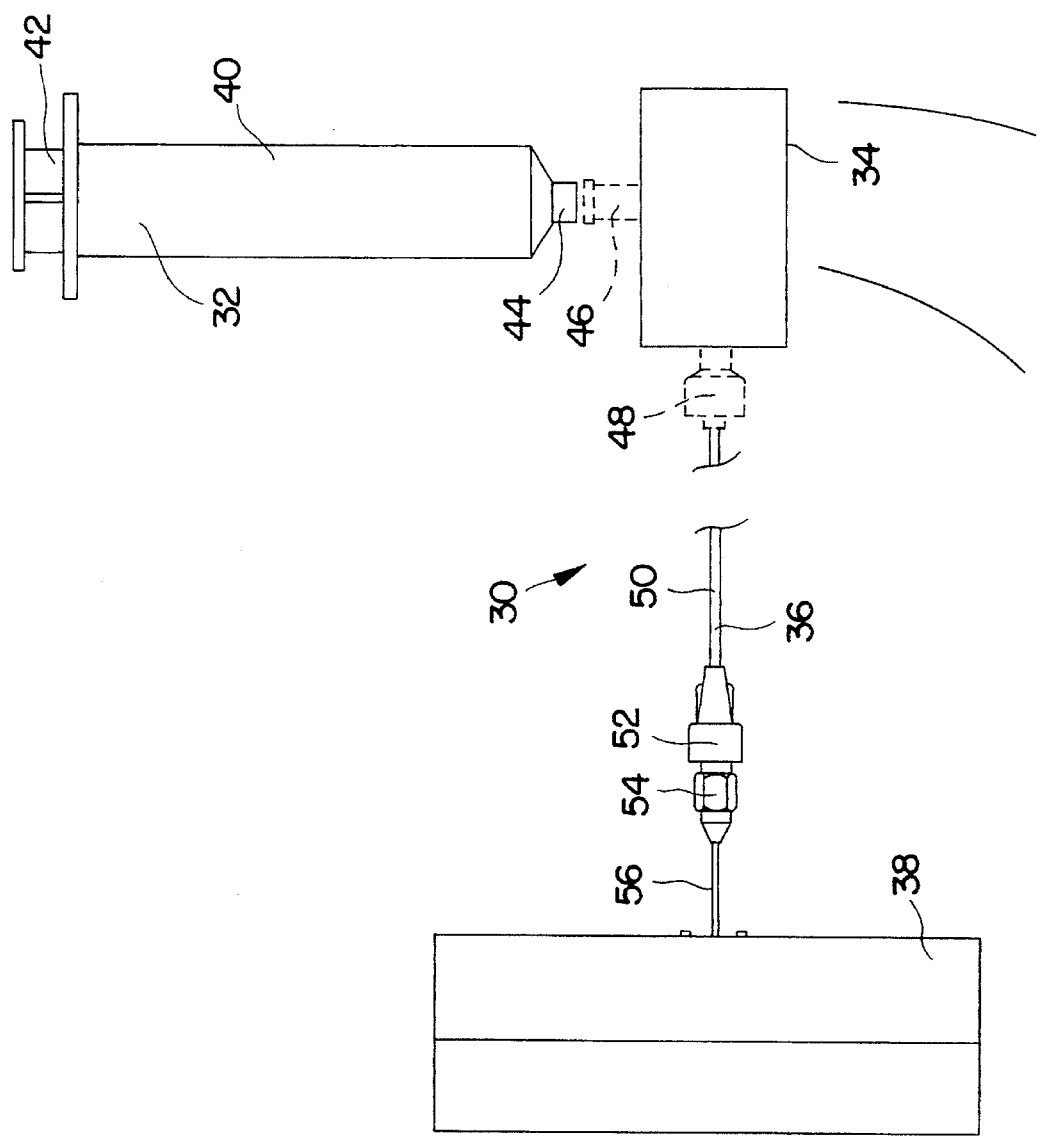
FIG. 2 depicts an exemplary preferred IDIP filling system in accordance with the present invention, depicted in a front view.

FIG. 2 depicts an exemplary preferred embodiment of an IDIP filling system 30 that includes a filling syringe 32, a pressure control valve 34, a filling tube 36, and an IDIP 38. The syringe 32 is of the type ordinarily used in the medical field and typically comprises a housing 40 with a plunger 42 slidably disposed therein. The size and type of syringe utilized will depend upon the amount of drug to be delivered to the pump 38. However, a 20 cc capacity syringe will typically be used. In preparation for coupling to the pressure control valve 34, the filling syringe 32 is filled with the particular drug or agent to be delivered to the pump 38.

After the syringe 32 has been filled, the discharge end 44 of the syringe 32 is coupled to the inlet orifice 46 of the pressure control valve 34. The inlet orifice 46 is preferably cylindrical and sized to sealingly couple to the discharge end 44 of the syringe 32. As the plunger 42 of the syringe 32 is depressed, the drug flows from the syringe 32 through the discharge end 44 and into the inlet orifice 46. The drug then passes through the pressure control valve 34 and exits into the filling tube 36 via a discharge coupling 48 on the pressure control valve 34. The discharge coupling 48 is configured to sealingly couple to the filling tube 36.

The filling tube 36 comprises a section 50 that runs from the discharge coupling 48 to a male coupling 52. The section 50 is shown cut away for illustration purposes. The male coupling 52 is, in turn, coupled to a female coupling 54. The female coupling 54 is, in turn, coupled to a hypodermic needle 56. The length of the hypodermic needle 56 is ordinarily substantially shorter than the length of the section 50 of the filling tube 36. The hypodermic needle 56 is coupled to the pump 38.

The pump 38 may be any of a variety of implantable drug infusion pumps such as, for example, a SynchroMed® pump, Model 8615, manufactured by Medtronic, Inc., Minneapolis, Minn. While an implantable pump 38 is depicted, it should be understood to those skilled in the art that the device used to deliver agent may be either implanted or extracorporeal.

Figure 3:
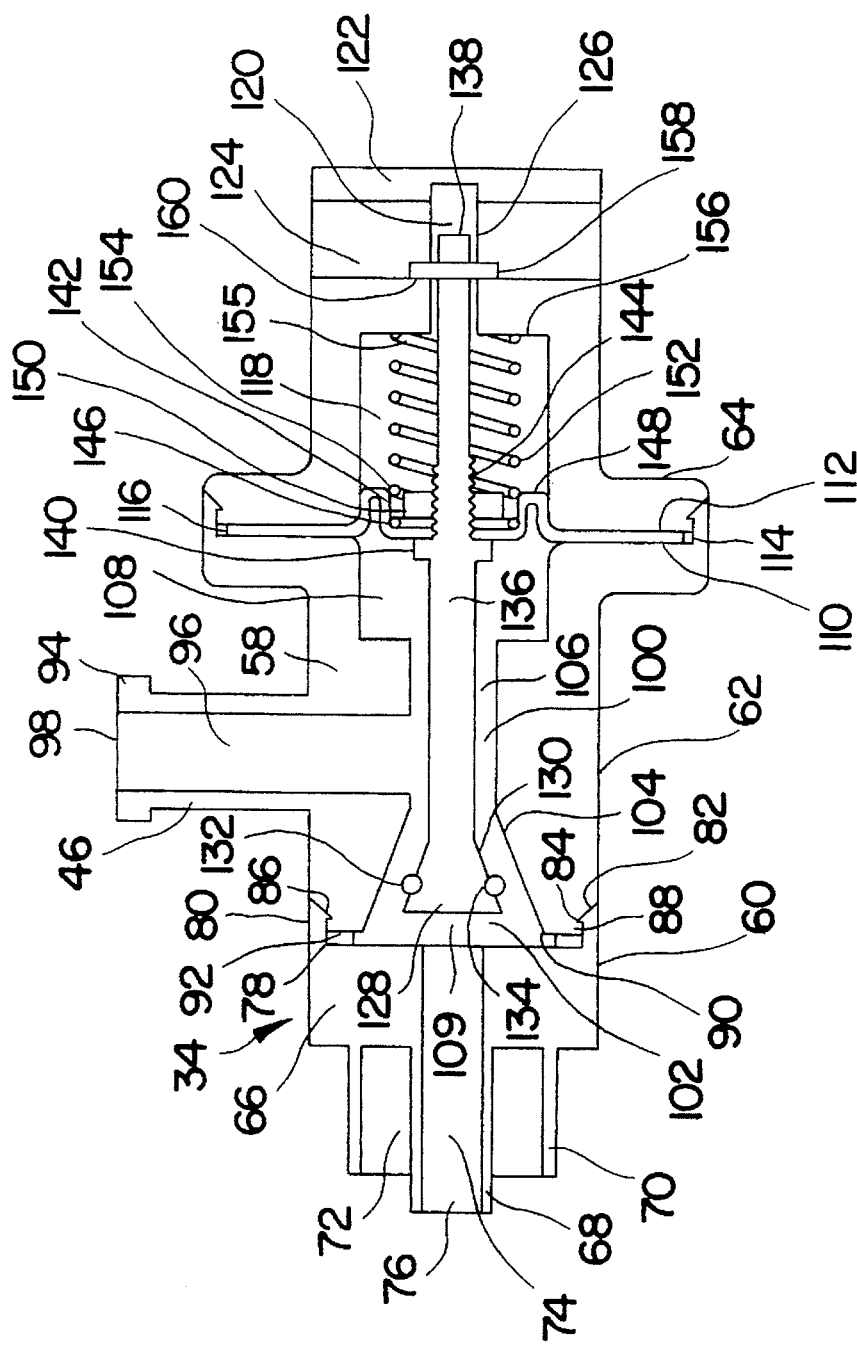
FIG. 3 depicts a detailed view of a pressure control valve, shown in an open position, for the exemplary preferred IDIP filling system, illustrated in half-section.
Figure 4:
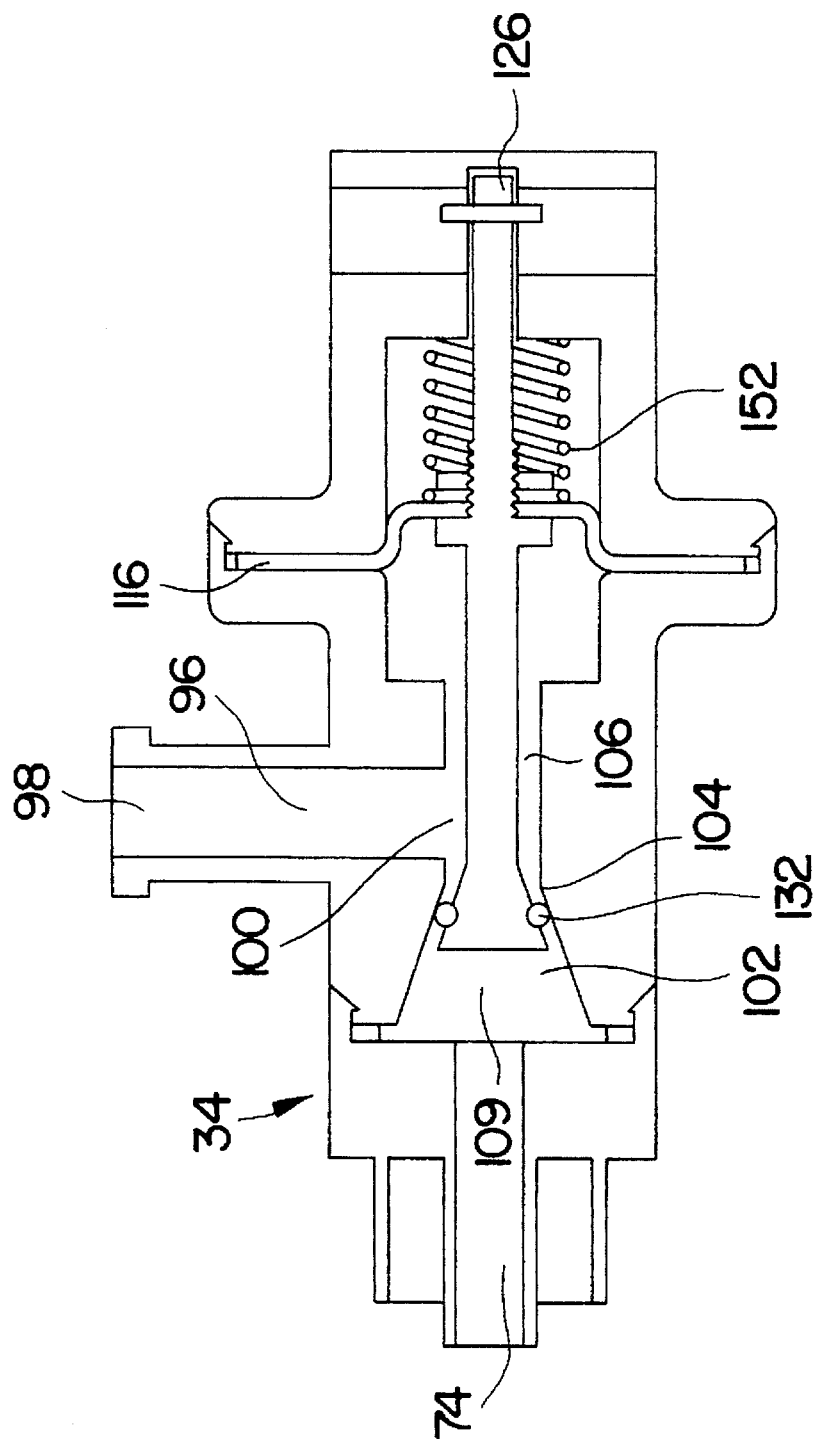
FIG. 4 depicts a detailed view of a pressure control valve, shown in a closed position, for the exemplary preferred IDIP filling system, illustrated in half-section.

The detailed structure of the pressure control valve 34 may be understood by reference to FIGS. 3 and 4, which show respectively, enlarged half-section views of the pressure control valve 34 in a normally open and a closed position. The pressure control valve 34 includes a valve body 58 which is divided into three sections, that for illustration purposes, may be referred to as a left section 60, a middle section 62 and a right section 64. The valve body is preferably fabricated from a polycarbonate material, such as, for example, a general purpose injection molding grade GE Lexan 121. Polycarbonate is desirable due both to its light weight and ease of molding.

The left section 60 comprises a cylindrical portion 66 that has, at one end, a tapered Luer fitting nipple 68 that is adapted to couple either to the discharge coupling 48 or directly to the hypodermic needle 36 shown in FIG. 2. Preferably, a Luer-Lock cylinder 70 is included to provide a more secure attachment to the filling tube 36. A cylindrical discharge passage 74 extends from the opening 76 of the Luer fitting 68 entirely through the left section 60.

The left section 60 is snap-coupled to the middle section 62. To achieve the snap-coupling, the cylindrical portion 66 terminates at its right end 78 in a relatively thin cylindrical shell 80. The distal end of the shell 80 has an inwardly beveled surface 82 that terminates in an inwardly facing spur 84. The left end of the middle section 62 has a beveled exterior surface 86 that terminates in a radially outwardly projecting shoulder 88. To achieve the snap-fit, the middle section 62 is pressed into the left section 60. As the shoulder 88 encounters the beveled surface 82, the cylindrical shell 80 is deformed radially outward until the radially projecting shoulder 88 clears the spur 84, at which time the cylindrical shell 80 snaps back to its normal position, enabling the spur 84 to snugly engage the shoulder 88. The cylindrical shell 80, the beveled surface 86, and the radially projecting shoulder 88 are sized to leave a gap 90 between the left section 60 and the radially projecting shoulder 88. A gasket 92 is disposed in the gap 90 to seal the interface between the cylindrical shell 80 and the middle section 62.

The middle section 62 has an inlet coupling 46, which is a female Luer fitting integrally formed with, and extending upward from, the middle section 62. The inlet coupling 46 preferably includes a Luer-Lock flange 94. An inlet passage 96 extends from the opening 98 in the inlet coupling 46 through a portion of the middle section 62, and terminates in a chamber 100 within the valve body 58. One end 102 of the chamber 100 has a generally frustoconical configuration due to the outward beveled interior surface 104 of the middle section 62. The chamber 100 is in fluid communication with the discharge passage 74. The central portion 106 of the chamber 100 is disposed within the middle section 62 and generally cylindrical. The chamber 100 terminates at its other end 108 in a generally cylindrical portion that is greater in diameter than the central portion 106. The combination of the inlet passage 96, the chamber 100, and the discharge passage 74 provides a flow passage 109 for a drug or agent to pass from the syringe 32 to the filling tube 36.

The right section 64 is snap-coupled to the middle section 62 in a manner that is identical to the snap-coupling between the left section 60 and the middle section 62. In this case, however, the middle section 62 has a substantially flat annular surface 110 that is disposed opposite a corresponding flat annular surface 112 on the right section 64. The right section 64 is snap-coupled to the middle section 62 to leave a gap 114 between the flat annular surface 110 and the flat annular surface 112.

A flexible membrane 116 is clamped between the flat annular surface 110 and the flat annular surface 112. The flexible membrane 116 isolates the chamber 100 from a cylindrical cell 118. The flexible membrane is preferably formed from an elastomeric material, such as, for example, ETR silicone, manufactured by Dow Corning. The flexible membrane 116 will be discussed in more detail below.

The cell 118 preferably has approximately the same diameter as the cylindrical portion 108 of the chamber 100. The cell 118 terminates at one end in a cylindrical bore 120 that extends from the cell 118 to, but not through, the end 122 of the right section 64. A slot 124 is vertically disposed in the right section 64 between the cell 118 and the end 122 of the right section 64. The slot 124 extends completely through the right section 64 and passes directly through the bore 120.

The flow passage 109 may be open or shut by a plunger or mandrel 126 slidably disposed within the valve body 58. One end 128 of the mandrel 126 has a generally frustoconical configuration with an exterior frustoconical surface 130 that has the same general bevel as the beveled surface 104. An O-ring 132 is snugly seated in a peripheral trough 134 that is formed in the frustoconical surface 130. The end 128 and the O-ring 132 are sized so that when the mandrel 126 is translated to the right as shown in FIG. 4, the O-ring 132 will sealingly engage the beveled surface 104 of the middle section 62, thereby shutting off the flow passage 109. The O-ring 132 is preferably formed from the same materials used to form the flexible membrane 116.

The middle portion 136 of the mandrel 126 is a generally elongated cylinder that passes through the flexible membrane 116 and terminates in a distal end 138 that is disposed within the bore 120. The mandrel 126 is sealingly coupled to the flexible membrane 116 by means of a radially projecting flange 140 that is formed integral with the mandrel 126. The flange 140 abuts the side of the flexible membrane exposed to the chamber 100. A nut 142 is disposed in the cell 118 and is threadedly attached to the mandrel 126 at 144. The nut 142 threadedly presses the flexible membrane 116 against the flange 140. A gasket 146 is sandwiched between the nut 142 and the side of the flexible membrane 116 that is exposed to the cell 118.

The mandrel 126 is preferably manufactured from a corrosion resistant material, such as, for example, 304 stainless steel. Other materials may be suitable as well, such as composite materials.

The flexible membrane 116 has an annular bulge 148 that projects into the cell 118. The internal diameter of the annular bulge 148 is slightly greater than the external diameter of the nut 142 and the gasket 146, thereby defining an annular space 150 between the annular bulge 148, and the nut 142 and the gasket 146.

A biasing member 152, depicted in this preferred embodiment as a coil spring, is disposed within the cell 118. One end 154 of the biasing member 152 bears against the flexible membrane 116 and is disposed in the annular space 150. The other end 155 of the biasing member 152 bears against the end surface 156 of the cell 118. The biasing member 152 biases the mandrel 126 to its normally open position as shown in FIG. 3. The biasing member 152 is designed to have a spring constant that is sufficient to enable the biasing member 152 to resist the force exerted on the flexible membrane 116 by the pressure of the fluid flowing through the flow passage 109, until that pressure exceeds a selected maximum value. That maximum pressure value will be the maximum pressure that can be tolerated by the pump 38. For example, in a preferred embodiment, the maximum allowable fluid pressure was found to be approximately 7 psi. A spring constant of approximately 2 pounds/inch was required to resist movement of the mandrel 126 and ultimate closure of the flow passage caused by a fluid pressure of 7 psi.

It should be understood to those skilled in the art that the size of the surface area of the flexible membrane 116 that is exposed to the chamber 100 should be tailored in conjunction with both the spring constant of the biasing member 152 and the surface area of the end 128 of the mandrel 126 that is opposed to the direction of fluid flow so that the mandrel 126 will move to a closed position when the preselected maximum pressure is reached.

To prevent the biasing member 152 from pushing the mandrel 126 past the normally open position shown in FIG. 3, a pin 158 is press-fit perpendicularly through the mandrel 126 proximate the distal end 138 thereof. The pin 158 bears against the shoulder surface 160 of the right section 64 that is exposed to the slot 124. The presence of the slot 124 provides a passage for air to enter or leave chamber 118, enabling the mandrel 126 to move back and forth within the bore 120.

Referring to FIGS. 2, 3, and 4, the pressure control valve 34 operates in the following manner. Assume for the purposes of this illustration, that the fluid flowing from the syringe 32 into the pressure control valve 34 is below the preselected maximum pressure rating for the pump 38. Under such circumstances, the pressure control valve 34 will operate in its normally open position as shown in FIG. 3. Fluid flows from the syringe 32 into the opening 98 and through the flow passage 109 defined by the inlet 96, the cylindrical and frustoconical portions 106 and 102 of the chamber 100 and the discharge passage 74. Assume now for the purposes of this illustration, that the pressure of the fluid flowing through the flow passage 109 exceeds the preselected maximum pressure. At that moment, the force of the fluid pressure bearing on the flexible membrane 116 will exceed the opposing force exerted by the biasing member 152.

As a result, the mandrel 126 will move to the right, as seen from FIG. 3, until the O-ring 132 contacts and seals against the beveled surface 104, thereby closing off the flow passage 109. The pressure control valve 34 is now in its fully closed position as shown in FIG. 4.

Figure 5:
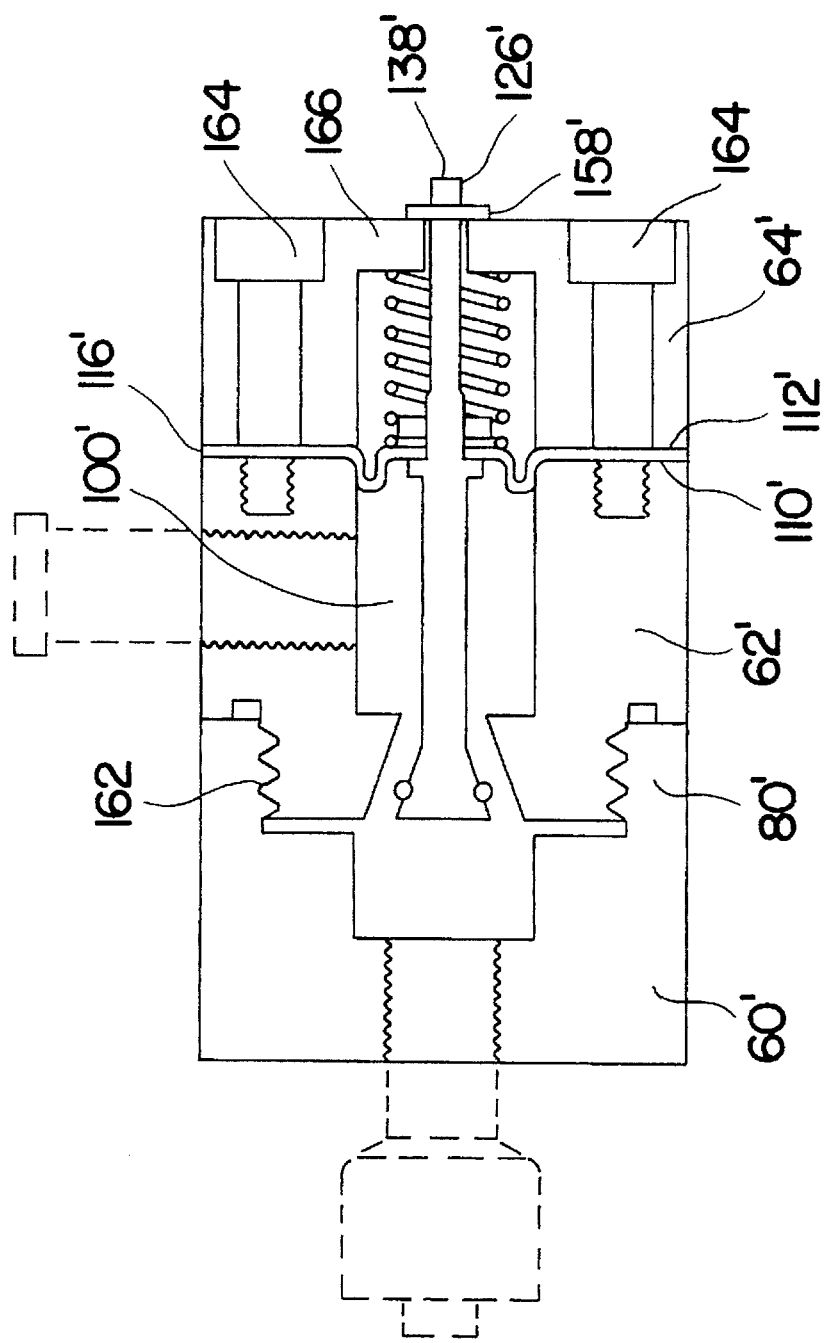
FIG. 5 depicts a detailed view of an alternate preferred embodiment of a pressure control valve shown in an open position, for an exemplary preferred IDIP filling system, illustrated in half-section.

In an alternate preferred embodiment depicted in FIG. 5, which is a half-section view of the pressure control valve 34', the various sections of the valve body 58' are connected in a slightly different fashion. The left section 60' again has a cylindrical shell 80', though in this preferred embodiment, the cylindrical shell 80' is threaded internally and adapted to threadedly connect to the externally threaded portion of the middle section 62' at 162.

An O-ring 163 is disposed between the left section 60' and the middle section 62' to prevent the leakage of fluid past the threaded connection at 162. The right section 64' and the middle section 62' are joined by bolts 164, which are preferably counter-sunk into the end surface 166 of the right section 64'. The middle section 62' and the right section 64' have respectively opposing, annular flat surfaces 110' and 112' that are separated by a flexible membrane 116'. In this alternate preferred embodiment, the annular bulge 148' in the flexible membrane 116' protrudes into the chamber 100'. Furthermore, the distal end 138' of the mandrel 126' and the pin 158' are located external to the valve body 58'. In all other respects, the structure and operation of this alternate preferred embodiment of the pressure control valve 34' is identical to the above-disclosed preferred embodiment.

Many modifications and variations may be made in the techniques and structures described and illustrated herein without departing from the spirit and scope of the present invention. For example, the filling tube 36 may be eliminated altogether and the pressure control valve 34 may be configured to couple directly to the IDIP 38 and may also be incorporated inside the IDIP. Accordingly, the techniques and structures described and illustrated herein should be understood to be illustrative only and not limiting upon the scope of the present invention.

What is claimed is:

1. A pressure controlled system for filling a drug infusion pump, comprising:

a filling syringe;

a pressure control valve coupled to said filling syringe and being in fluid communication therewith; said pressure control valve being adapted to couple to said drug infusion pump and comprising:

a valve body;

a flow passage extending through said valve body;

a flexible membrane disposed within said valve body; said flexible membrane having a surface in fluid communication with said flow passage; said flexible membrane being operable to expand and contract in response to pressure in said flow passage;

a mandrel coupled to said flexible membrane; said mandrel having a first open position and a second closed position; said mandrel being operable to move to said closed position to close said flow passage when said flexible membrane is expanded a preselected amount; and a biasing member being operable to bias said mandrel toward said open position.

2. A pressure controlled system according to claim 1, wherein a filling tube is coupled to said pressure control valve, said filling tube being adapted to couple to said pump.

3. A pressure controlled system according to claim 1, wherein said mandrel has a first end having a frustoconical exterior surface adapted to contact an interior frustoconical surface of said flow passage when said mandrel is in said closed position to close said flow passage.

4. The pressure control valve of claim 1 wherein said flexible membrane comprises a thin sheet of silicone rubber.

5. The pressure control valve of claim 1 wherein said biasing member comprises a coil spring disposed within said valve body.

6. The pressure control valve of claim 1 wherein said coil spring has a first end bearing against said flexible membrane and a second end bearing against said valve body.

7. A pressure controlled drug infusion pump filling system, comprising:

an infusion pump;

a filling syringe;

a pressure control valve coupled to said filling syringe and to said pump, said pressure control valve being in fluid communication with said pump and with said filling syringe; said pressure control valve comprising:

a valve body;

a flow passage extending through said valve body;

a flexible membrane disposed within said valve body; said flexible membrane having a surface in fluid communication with said flow passage; said flexible membrane being operable to expand and contract in response to pressure in said flow passage;

a mandrel coupled to said flexible membrane; said mandrel having a first open position and a second closed position; said mandrel being operable to move to said closed position to close said flow passage when said flexible membrane is expanded a preselected amount; and a biasing member being operable to bias said mandrel toward said open position.

8. A pressure controlled system according to claim 7, wherein a filling tube is coupled to said pressure control valve, said filling tube being adapted to couple to said pump.

9. A pressure controlled system according to claim 7, wherein said mandrel has a first end having a frustoconical exterior surface adapted to contact an interior frustoconical surface of said flow passage when said mandrel is in said closed position to close said flow passage.

10. The pressure control valve of claim 7 wherein said flexible membrane comprises a thin sheet of silicone rubber.

11. The pressure control valve of claim 7 wherein said biasing member comprises a coil spring disposed within said valve body.

12. The pressure control valve of claim 7 wherein said coil spring has a first end bearing against said flexible membrane and a second end bearing against said valve body.

13. A method of filling a drug infusion pump with a fluid while preventing over-pressurization of said pump, comprising the steps of:

coupling a filling syringe containing a preselected amount of said fluid to the inlet of a pressure regulating valve;

coupling the outlet of said pressure regulating valve to a hypodermic needle;

inserting said hypodermic needle into said pump; and actuating said filling syringe to pass fluid through said pressure regulating valve and into said pump until the pressure of said fluid passing through said pressure regulating valve achieves a preselected maximum at which time said pressure regulating valve closes to prevent further flow of fluid into said pump.

* * * * *